United States Patent
Berenbaum et al.

(10) Patent No.: US 10,571,438 B2
(45) Date of Patent: Feb. 25, 2020

(54) STRUCTURAL HEALTH MONITORING AND BASELINE DEVIATION ASSESSMENT

(71) Applicant: Simmonds Precision Products, Inc., Vergennes, VT (US)

(72) Inventors: Arthur Berenbaum, Addison, VT (US); Travis Gang, Hinesburg, VT (US); Peter J. Carini, Underhill, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 190 days.

(21) Appl. No.: 15/618,831

(22) Filed: Jun. 9, 2017

(65) Prior Publication Data
US 2018/0356372 A1    Dec. 13, 2018

(51) Int. Cl.
*G01N 29/44*    (2006.01)
*G01M 5/00*    (2006.01)
*G01N 29/04*    (2006.01)
*G01N 29/22*    (2006.01)

(52) U.S. Cl.
CPC ...... *G01N 29/4445* (2013.01); *G01M 5/0016* (2013.01); *G01M 5/0066* (2013.01); *G01N 29/043* (2013.01); *G01N 29/227* (2013.01); *G01N 29/228* (2013.01)

(58) Field of Classification Search
CPC ............. G01N 29/4445; G01N 29/043; G01N 29/227; G01N 29/228; G01M 5/0016; G01M 5/0066
USPC .......................................................... 73/645
See application file for complete search history.

(56) References Cited

U.S. PATENT DOCUMENTS

| 4,901,575 | A | 2/1990 | Bohannan et al. |
| 7,366,627 | B2 | 4/2008 | Gordon et al. |
| 7,809,513 | B2 | 10/2010 | Beard et al. |
| 2002/0036276 | A1* | 3/2002 | Seeman ............... G01N 21/85 250/573 |

(Continued)

FOREIGN PATENT DOCUMENTS

WO    WO2015195184 A2    12/2015

OTHER PUBLICATIONS

Extended European Search Report for European Patent Application No. 18176249.3, dated Nov. 2, 2018, 8 pages.

*Primary Examiner* — Suman K Nath
(74) *Attorney, Agent, or Firm* — Kinney & Lange, PA

(57) ABSTRACT

At least one baseline structural interrogation of a physical structure is performed in one or more corresponding baseline conditions of the structure. The one or more baseline conditions are stored, and one or more current conditions are sensed. It is determined whether a difference between the one or more current conditions and the one or more baseline conditions satisfies at least one threshold deviation criterion. A current structural interrogation of the structure is performed in response to determining that the difference between the one or more current conditions and the one or more baseline conditions satisfies the least one threshold deviation criterion. An indication that the at least one threshold deviation criterion is not satisfied is output in response to determining that that the difference between the one or more current conditions and the one or more baseline conditions does not satisfy the at least one threshold deviation criterion.

15 Claims, 2 Drawing Sheets

(56) References Cited

U.S. PATENT DOCUMENTS

2005/0075769 A1* 4/2005 Eschborn .......... G05B 23/0254
701/33.4
2009/0306907 A1 12/2009 Ihn et al.
2016/0266717 A1 9/2016 Oral et al.

* cited by examiner

STRUCTURAL HEALTH MONITORING AND BASELINE DEVIATION ASSESSMENT

BACKGROUND

The present disclosure relates generally to health monitoring, and in particular to Structural Health Monitoring baseline deviation assessments.

Structural Health Monitoring (SHM) systems have been utilized for the detection and characterization of damage within structures. For example, acousto-ultrasonic SHM techniques involve the interrogation of structures to identify damage by inducing vibrations within the structural material and monitoring the vibrational response. Such damage, often defined as changes to the material and/or geometric properties of a structural system which negatively impact the performance of the system, can be detected based on comparisons of the vibrational response of the structure in multiple states. For example, a structure is often first interrogated when the structure is in a known, defect-free condition, to establish a baseline vibrational response. Results of subsequent acousto-ultrasonic interrogations are compared to the baseline response to identify changes in the structure that may indicate damage.

Vibrational response of the structure is dependent upon environmental variables, such as temperature, mechanical strain, or other such variables. For instance, increased temperature of a structure results in expansion of the structural material and a corresponding change in the vibrational response of the structure to the acousto-ultrasonic interrogation. Comparison of interrogation results taken under the same or similar conditions can enable accurate damage assessments of the structure. Comparison of interrogation results at different conditions (e.g., temperatures, strains, etc.) can produce inaccurate damage assessments, thereby reducing the dependability, reliability, and effectiveness of the SHM system.

SUMMARY

In one example, a method includes performing at least one baseline structural interrogation of a physical structure in one or more corresponding baseline conditions of the structure, and storing, by a controller, the one or more baseline conditions of the structure corresponding to the at least one baseline structural interrogation. The method further includes sensing, using at least one sensor, one or more current conditions of the structure, and determining, by the controller, whether a difference between the one or more current conditions and the one or more baseline conditions satisfies at least one threshold deviation criterion. The method further includes performing a current structural interrogation of the structure in response to determining that the difference between the one or more current conditions and the one or more baseline conditions satisfies the at least one threshold deviation criterion. The method further includes outputting, by the controller, an indication that the at least one threshold deviation criterion is not satisfied in response to determining that that the difference between the one or more current conditions and the one or more baseline conditions does not satisfy the at least one threshold deviation criterion.

In another example, a system includes a physical structure, one or more sensors configured to sense current conditions of the structure, one or more transducers configured to perform a structural interrogation of the structure by inducing ultrasonic vibrations in the structure and sensing a resulting vibrational response of the structure, and a controller. The controller is configured to store one or more baseline conditions of the structure corresponding to at least one baseline structural interrogation of the structure, receive one or more current conditions of the structure sensed by the one or more sensors, and determine whether a difference between the one or more current conditions and the one or more baseline conditions satisfies at least one threshold deviation criterion. The controller is further configured to perform a current structural interrogation of the structure via the one or more transducers in response to determining that the difference between the one or more current conditions and the one or more baseline conditions satisfies the at least one threshold deviation criterion. The controller is further configured to output an indication that the at least one threshold deviation criterion is not satisfied in response to determining that the difference between the one or more current conditions and the one or more baseline conditions does not satisfy the at least one threshold deviation criterion.

DETAILED DESCRIPTION

As described herein, a Structural Health Monitoring (SHM) system for, e.g., an aircraft, utilizes multiple baseline interrogations for each of one or more structures (e.g., components of the aircraft) taken under multiple monitoring regimes corresponding to different environmental and/or operating conditions of each of the components. Such conditions can include, e.g., varying temperatures, varying mechanical loads, or other conditions that can affect a response of the structure to a structural interrogation, such as a vibrational response to an acousto-ultrasonic interrogation. The baseline conditions for each component are stored in relation to the results of the corresponding interrogation. Sensors at or near the corresponding structures monitor current conditions of the structure, such as a current temperature, a current strain, or other current conditions. The current conditions are compared with the stored baseline conditions to determine whether the current conditions and the stored baseline conditions are comparable to enable accurate damage assessments of the structure.

If the conditions are comparable (e.g., within a threshold deviation), a current structural interrogation is performed (e.g., in response to user input requesting the interrogation) and the results are compared with a set of baseline results corresponding to a stored set of conditions that are most closely related to the current conditions of the component. If the conditions are not comparable (e.g., exceeding the threshold deviation), an indication of the deviation is output via, e.g., a user interface or other output device. In some examples, the output can include an extent of the deviation, such as an extent of the deviation from an acceptable temperature range or other conditional parameters.

Accordingly, a SHM system implementing techniques of this disclosure can increase accuracy of structural damage assessments by comparing results of a current structural interrogation with baseline results that correspond to environmental and/or operating conditions that are similar to (e.g., within a threshold deviation from) current conditions of the structure. Moreover, the SHM system as described herein provides outputs to the user regarding the current conditions of the structure and whether such conditions are comparable to baseline conditions to enable accurate analysis and damage assessments. As such, the techniques of this disclosure increase accuracy of structural health monitoring as well as user awareness of whether current conditions of the structure are sufficient to enable accurate structural analysis.

Figure 1:
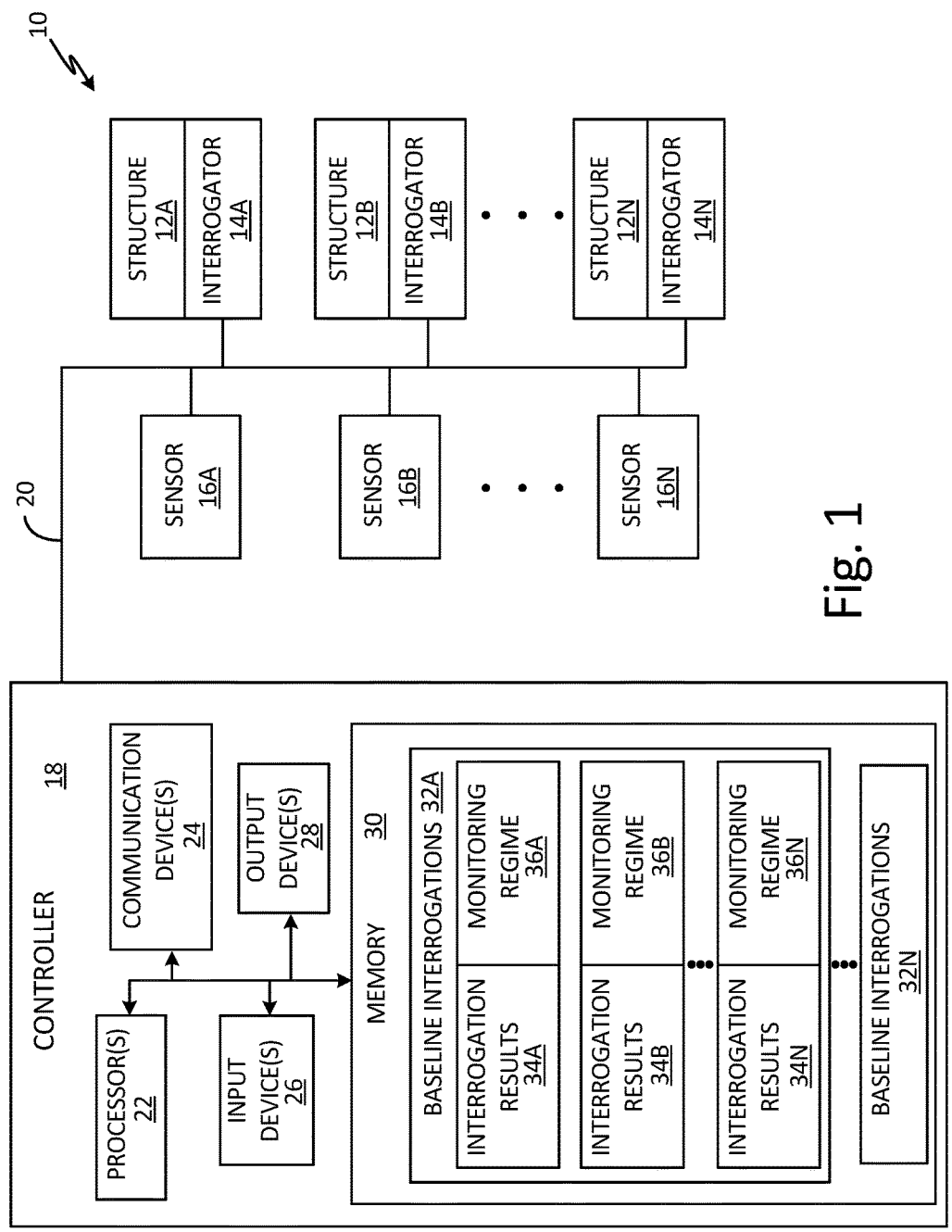
FIG. 1 is a block diagram illustrating an example aircraft system that performs structural health monitoring.

FIG. 1 is a block diagram illustrating structural health monitoring (SHM) system 10 that performs structural interrogations of structures 12A-12N. As illustrated in FIG. 1, SHM system 10 further includes interrogators 14A-14N, sensors 16A-16N, controller 18, and communications data bus 20. Controller 18 includes one or more processors 22, one or more communication devices 24, one or more input devices 26, one or more output devices 28, and computer-readable memory 30. Computer-readable memory 30 stores baseline interrogations 32A-32N. Each of baseline interrogations 32A-32N stores the results of one or more structural interrogations in relation to an associated monitoring regime (e.g., representing conditions such as temperature, strain, or other environmental and/or operating conditions) for one of structures 12A-12N. That is, baseline interrogations 32A stores interrogation results 34A-34N and associated monitoring regimes 36A-36N corresponding to baseline structural interrogations of structure 12A. Similarly, though not illustrated in FIG. 1, baseline interrogations 32N stores interrogation results and associated monitoring regimes corresponding to baseline structural interrogations of structure 32N. In general, baseline interrogations 32A-32N each store one or more interrogation results and associated monitoring regimes for one of structures 12A-12N, such that each one of baseline interrogations 32A-32N corresponds to one of structures 12A-12N.

Each of structures 12A-12N can be a physical structure, component, or other physical element in which it is desirable to detect defects, such as cracks, deformation, or other structural defects. Structures 12A-12N can be, for example, aircraft components such as airfoils, casings, pylons, or any other component, structure, or part of a structure. Interrogators 14A-14N can be, for example, transducers configured to perform a structural interrogation by inducing ultrasonic waves within a respective structure 12A-12N and measure a vibrational response as a result of the corresponding interrogation. Sensors 16A-16N can be any one or more analog or digital device capable of sensing environmental parameters of structures 12A-12N and/or the environment in which structures 12A-12N reside. For instance, sensors 16A-16N can be any one or more of temperature sensors, strain sensors, pressure sensors, or system sensors (e.g., aircraft system sensors) configured to provide signals indicative of system operational states, such as weight-on-wheels, power-up, power-down, altitude, airspeed, engine status, or other system and/or environmental data. While illustrated as including "N" structures, interrogators, and sensors, it should be understood that the variable "N" as used herein denotes any arbitrary number. As such, system 10 can include any one or more structures 12A-12N, any one or more interrogators 14A-14N, and any one or more sensors 16A-16N. Similarly, memory 30 of controller 18 can store any number of baseline interrogations 32A-32N, and each of baseline interrogations 32A-32N can store any number of interrogation results 34A-34N and associated monitoring regimes 36A-36N. It should also be appreciated that the number represented by the variable "N" need not be the same for each of structures 12A-12N, interrogators 14A-14N, sensors 16A-16N, baseline interrogations 32A-32N, interrogation results 34A-34N, and monitoring regimes 36A-36N.

As illustrated in FIG. 1, controller 18 is communicatively coupled with interrogators 14A-14N and sensors 16A-16N via communications data bus 20. Communications data bus 20 can be any wired or wireless data bus utilized to facilitate communication between interrogators 14A-14N, sensors 16A-16N, and controller 18. For instance, communications data bus 20 can be a RS232, RS485, or other physical data bus. In some examples, communication between any one or more of interrogators 14A-14N, sensors 16A-16N, and controller 18 can be performed wirelessly. Controller 18, in some examples, is an on-board electronics device disposed on an aircraft or other vehicle that includes structures 12A-12N. In other examples, controller 18 can be a remote device, such as a ground-based or otherwise remote device that is separate from an aircraft or other vehicle that includes structures 12A-12N. In certain examples, aspects of this disclosure attributed to controller 18 can be distributed among two or more on-board and/or off-board (e.g., remote) devices.

Controller 18, as illustrated in FIG. 1, includes one or more processors 22. Processors 22 are configured to implement functionality and/or process instructions for execution within controller 18. For instance, processors 22 can be capable of processing instructions stored in computer-readable memory 30. Examples of processors 22 can include any one or more of a microprocessor, a controller, a digital signal processor (DSP), an application specific integrated circuit (ASIC), a field-programmable gate array (FPGA), or other equivalent discrete or integrated logic circuitry.

Controller 18 utilizes one or more communication devices 24 to communicate with external devices via one or more communicative connections, such as with any one or more of interrogators 14A-14N and sensors 16A-16N via communications data bus 20. Communications devices 24 can be a network interface card, such as an Ethernet card, an optical transceiver, a radio frequency transceiver, or any other type of device that can send and receive information. Other examples of such network interfaces can include Bluetooth, 3G, 4G, WiFi radio interfaces, and Universal Serial Bus (USB).

Controller 18, as illustrated in FIG. 1, also includes one or more input devices 26. Input devices 26, in some examples, are configured to receive input from a user. Examples of input devices 26 can include a mouse, a keyboard, a microphone, a camera device, a presence-sensitive and/or touch-sensitive display, a tablet computer, a smart phone, or other type of device configured to receive input from a user. One or more output devices 28 can be configured to provide output to a user. Examples of output devices 28 can include a display device, a sound card, a video graphics card, a speaker, a cathode ray tube (CRT) monitor, a Light Emitting Diode (LED) display, a liquid crystal display (LCD), a tablet, a smart phone, or other type of device for outputting information.

Computer-readable memory 30 can be configured to store information within controller 18 during operation. Computer-readable memory 30, in some examples, is described as a computer-readable storage medium. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). Computer-readable memory 30 can include volatile and/or non-volatile memory elements. Examples of volatile memories can include random access memories (RAM), dynamic random access memories (DRAM), static random access memories (SRAM), and other forms of volatile memories. Examples of non-volatile memories include magnetic hard discs, optical discs, floppy discs, flash memories, or forms of electrically programmable memories (EPROM) or electrically erasable and programmable (EEPROM) memories.

As illustrated in FIG. 1, memory 30 stores baseline interrogations 32A-32N, each including one or more interrogation results (e.g., interrogation results 34A-34N) and associated monitoring regimes (e.g., monitoring regimes 36A-36N). Interrogation results represent results of a structural interrogation, such as vibrational frequencies, phases, amplitudes, or other vibrational results of acousto-ultrasonic interrogations performed via interrogators 14A-14N. Monitoring regimes represent environmental and/or operating conditions of structures 12A-12N during each of the associated interrogations. Such conditions include, e.g., temperature, strain, pressure, aircraft or other vehicle operating state, or other environmental and/or operating conditions.

Each of baseline interrogations 32A-32N corresponds to one of structures 12A-12N. For instance, baseline interrogations 32A can correspond to structure 12A, and baseline interrogations 32N can correspond to structure 12N, such that each one of baseline interrogations 32A-32N corresponds to one of structures 12A-12N. Interrogation results 34A-34N represent the results of "N" structural interrogations of structure 12A, each at a corresponding one of monitoring regimes 36A-36N. That is, interrogation results 34A represent the results of a structural interrogation of structure 12A at the environmental and/or operating conditions represented by monitoring regime 36A. Interrogation results 34B represent the results of a structural interrogation of structure 12A at the environmental and/or operating conditions represented by monitoring regime 36B, and interrogation results 34N represent the results of a structural interrogation of structure 12N at the environmental and/or operating conditions represented by monitoring regime 12N.

Each of monitoring regime 36A-36N represent different operating and/or environmental conditions of structure 12A. As such, baseline interrogations 32A store interrogation results 34A-34N of structure 12A, each associated with one of the differing environmental and/or operating conditions represented by monitoring regimes 36A-36N. Similarly, baseline interrogations 32N store interrogation results of structure 12N, each of the interrogation results associated with one of differing environmental and/or operating conditions represented by the associated monitoring regimes. Accordingly, memory 30 stores baseline interrogations 32A-32N that include results of structural interrogations of structures 12A-12N at differing environmental and/or operating conditions.

In operation, controller 18 presents a user interface at output devices 28 (e.g., a display device) and receives user input via input devices 26 (e.g., a touch-sensitive display, a keyboard, a mouse, or other input devices). The user interface presented by controller 18 enables user input to request a structural interrogation of any one or more of structures 12A-12N. For instance, a maintenance technician or other user can interface with controller 18 via the user interface during on-ground maintenance activities of an aircraft including structures 12A-12N. Controller 18 receives data from sensors 16A-16N regarding current conditions (e.g., current temperature, current strain, current aircraft operational state, or other current conditions) of structures 12A-12N.

Controller 18 compares the current conditions of structures 12A-12N to the baseline conditions represented by the monitoring regimes stored at the corresponding one of baseline interrogations 32A-32N. For example, in response to a request for a structural interrogation of structure 12A, controller 18 can compare current conditions sensed by any one or more of sensors 16A-16N to the baseline conditions represented by monitoring regimes 36A-36N.

Controller 18 determines whether a difference between the current conditions sensed by sensors 16A-16N and the baseline conditions represented by monitoring regimes 36A-36N satisfy at least one threshold deviation criterion. The threshold deviation criterion can include, e.g., a maximum deviation of any one or more of the current conditions from the baseline conditions of monitoring regimes 36A-36N. For instance, the threshold deviation criterion can include a maximum temperature deviation, a maximum strain deviation, or other such deviation criterion between a sensed temperature, strain, or other current condition of structure 12A and a corresponding temperature, strain, or other condition associated with any one or more of monitoring regimes 36A-36N.

In some examples, controller 18 can store the one or more threshold deviation criterion, such as at computer-readable memory 30. In other examples, controller 18 can receive the one or more threshold deviation criterion via the user interface, such as via input devices 26. The threshold deviation criterion can be determined (e.g., empirically) as a maximum deviation of the corresponding conditions that enable accurate damage assessment based on the results of the comparison of a current structural interrogation to the baseline interrogation results. The one or more threshold deviation criterion can be a same or different criterion for any one or more of structures 12A-12N.

In response to determining that the threshold deviation criterion is not satisfied (e.g., the deviation exceeds the maximum deviation criterion), controller 18 can output an indication that the threshold deviation criterion is not satisfied, such as via output devices 28 (e.g., a display device, a speaker device, or other output device). In certain examples, the output indication that the threshold deviation criterion is not satisfied can include an indication of an extent by which the threshold deviation criterion is not satisfied, such as the amount by which any one or more of the current conditions deviates from a threshold value, range, or other deviation criterion.

In some examples, controller 18 can refrain from performing the requested current structural interrogation in response to determining that the one or more threshold deviation criterion are not satisfied. In other examples, controller 18 can perform the requested current structural interrogation even when the one or more threshold deviation criterion are not satisfied, but may indicate that the requested structural interrogation was performed under current conditions that did not satisfy the one or more threshold deviation criterion. In certain examples, controller 18 can output a notification that the one or more threshold deviation criterion are not satisfied, and can perform the current structural interrogation in response to receiving user input (e.g., via the user interface) acknowledging that the one or more threshold deviation criterion are not satisfied and requesting that the current structural interrogation be performed regardless. In some examples, controller 18 can receive user input (e.g., via the user interface) to perform a current structural interrogation and include the results of the structural interrogation to the baseline conditions represented by monitoring regimes 36A-36N, e.g., by adding a new monitoring regime corresponding to current conditions as one of monitoring regimes 36A-36N and storing the structural interrogation results as a corresponding one of interrogation results 34A-34N). Accordingly, in response to an indication that the one or more threshold deviation criterion are not satisfied, a user can provide input to cause controller 18 to perform a structural interrogation and store the results in association with current conditions, thereby effectively including the current monitoring conditions with the baseline data.

In response to determining that the one or more threshold deviation criterion are satisfied (e.g., the deviation does not exceed a maximum deviation criterion), controller 18 can perform a current structural interrogation of any one or more of structures 12A-12N. For example, controller 18 can transmit control commands (e.g., electrical and/or communicative commands) to any one or more of interrogators 14A-14N to induce ultrasonic waves within a respective structure 12A-12N and measure a vibrational response as a result of the corresponding interrogation.

Results of the current structural interrogation can be stored and/or analyzed by controller 18 and/or a separate device communicatively coupled with controller 18 (e.g., a ground-based controller device in wireless or wired communication with controller 18) to identify damage or other defects of any one or more of structures 12A-12N. Analysis of the results of the current structural interrogation can include comparison of the current results to one of the baseline interrogation results associated with the monitoring regime that most closely resembles the sensed current conditions. For instance, controller 18 can compare the sensed current conditions (e.g., temperature, strain, or other current conditions) of structure 12A to monitoring regimes 36A-36N to identify one of monitoring regimes 36A-36N representing baseline conditions that are nearest to (e.g., a least deviation from) the sensed current conditions. Controller 18 can, in such examples, compare results of the current structural interrogation of structure 12A to the one of interrogation results 34A-34N that is associated with the identified one of monitoring regimes 36A-36N. In some examples, controller 18 can compare the results of the current structural interrogation to interpolated results between multiple sets of interrogation results 34A-34N, such as based on a deviation of the current conditions from multiple ones of monitoring regimes 36A-36N. In response to identifying damage or other defect to one or more of structures 12A-12N, controller 18 can output an indication of the identified damage and/or the identified structures 12A-12N having the defect.

Accordingly, SHM system 10, implementing techniques of this disclosure can increase an accuracy of structural damage assessments of structures 12A-12N by comparing results of a current structural interrogation with interrogation results of stored baseline interrogations 32A-32N that were obtained under comparable (e.g., within a threshold deviation from) conditions, such as temperature, strain, aircraft operating state, or other conditions. In addition, SHM system 10 as described herein provides output to the user via a user interface presented by controller 18 to alert the user of the current conditions of structures 12A-12N and whether such conditions are comparable to stored baseline conditions to enable accurate damage assessments.

Figure 2:
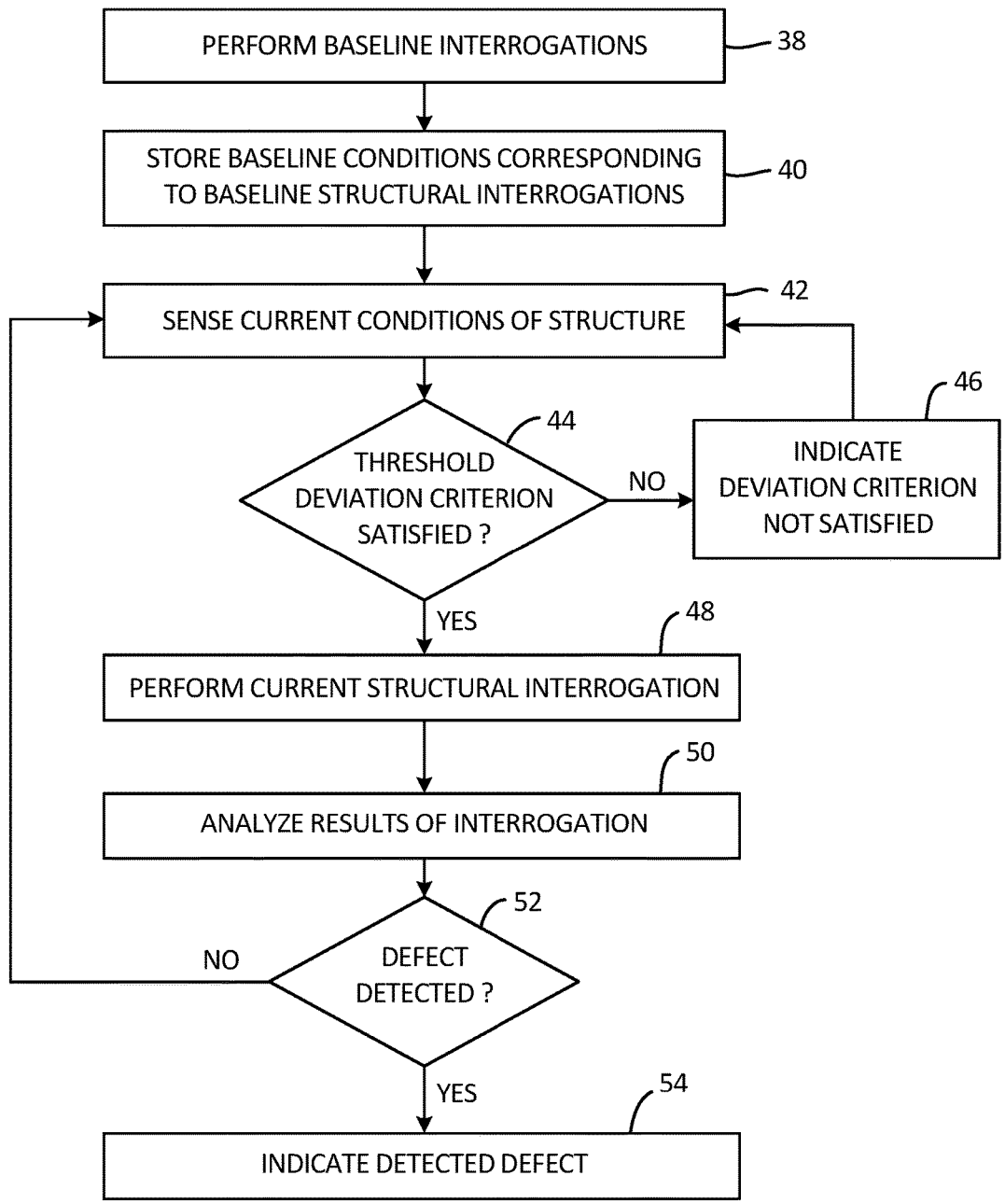
FIG. 2 is a flow diagram illustrating example operations to perform structural health monitoring.

FIG. 2 is a flow diagram illustrating example operations to perform structural health monitoring. The example operations of FIG. 2 are described below within the context of SHM system 10 of FIG. 1 for purposes of clarity and ease of discussion.

As illustrated in FIG. 2, at least one baseline structural interrogation of a physical structure can be performed in one or more corresponding baseline conditions of the structure (Step 38). For instance, controller 18 can perform one or more baseline interrogations of any one or more of structures 12A-12N via interrogators 14A-14N. The one or more baseline interrogations can be performed at varying baseline conditions corresponding to, e.g., monitoring regimes 36A-36N or other monitoring regimes associated with any one or more of baseline interrogations of structures 12A-12N.

The one or more baseline conditions of the structure corresponding to the at least one baseline structural interrogation can be stored (Step 40). For example, controller 18 can store monitoring regimes (e.g., monitoring regimes 36A-36N) for each of baseline interrogations 32A-32N. Current conditions of the structure can be sensed (Step 42). For instance, sensors 16A-16N can sense current conditions (e.g., temperature, strain, aircraft operating state, or other conditions) for any one or more of structures 12A-12N.

It can be determined whether a difference between the one or more current conditions and the one or more baseline conditions satisfies at least one threshold deviation criterion (Step 44). As an example, controller 18 can determine whether a difference between sensed current conditions of structure 12A and baseline conditions represented by monitoring regimes 36A-36N exceed a maximum threshold deviation. In response to determining that the at least one threshold deviation criterion is not satisfied ("NO" branch of Step 44), an indication that the at least one threshold deviation criterion is not satisfied can be output (Step 46). For instance, controller 18 can output an indication that the at least one threshold deviation criterion is not satisfied via output devices 28 (e.g., presenting a graphical user interface). In some examples, the indication that the at least one threshold deviation criterion is not satisfied can include an indication of an extent by which the threshold deviation criterion is not satisfied.

In response to determining that the at least one threshold deviation criterion is satisfied ("YES" branch of 44), a current structural interrogation of the structure can be performed (Step 48). For example, controller 18 can perform a current structural interrogation of any one or more of structures 12A-12N via one or more of interrogators 14A-14N. It can be determined whether structural damage or other defect is present within the structure (Step 52). For instance, controller 18 can compare the results (e.g., the vibrational response) of the current structural interrogation to an identified one of the stored baseline interrogation results to identify the presence of damage or other defect within one or more of structures 12A-12N.

In response to determining that no damage or defect is identified ("NO" branch of Step 52), the current conditions of the structure can continue to be sensed (Step 42). In response to determining that damage or other defect is present in the structure, an indication of the identified defect or other damage can be output (Step 54). For example, controller 18 can output an indication of the presence of the identified damage or other defect within one or more of structures 12A-12N via output devices 28.

Accordingly, techniques of this disclosure can increase accuracy of structural damage assessments by comparing results of a current structural interrogation with baseline results that correspond to environmental and/or operating conditions that are within a threshold deviation from current conditions of the structure. In addition, the techniques can increase user awareness through output indications of whether the current conditions of the structure are sufficiently comparable to stored baseline conditions to enable accurate structural analysis.

Discussion of Possible Embodiments

The following are non-exclusive descriptions of possible embodiments of the present invention.

A method includes performing at least one baseline structural interrogation of a physical structure in one or more corresponding baseline conditions of the structure, and storing, by a controller, the one or more baseline conditions of the structure corresponding to the at least one baseline structural interrogation. The method further includes sensing, using at least one sensor, one or more current conditions of the structure, and determining, by the controller, whether a difference between the one or more current conditions and the one or more baseline conditions satisfies at least one threshold deviation criterion. The method further includes performing a current structural interrogation of the structure in response to determining that the difference between the one or more current conditions and the one or more baseline conditions satisfies the least one threshold deviation criterion. The method further includes outputting, by the controller, an indication that the at least one threshold deviation criterion is not satisfied in response to determining that that the difference between the one or more current conditions and the one or more baseline conditions does not satisfy the at least one threshold deviation criterion.

The method of the preceding paragraph can optionally include, additionally and/or alternatively, any one or more of the following features, configurations, operations, and/or additional components:

The one or more baseline conditions can include a temperature of the structure corresponding to the at least one baseline structural interrogation. The one or more current conditions can include a current temperature of the structure.

The at least one threshold deviation criterion can include a maximum deviation between the one or more baseline conditions of the structure and the one or more current conditions of the structure.

Performing the at least one baseline structural interrogation of the structure can include performing a plurality of baseline structural interrogations of the structure in a plurality of corresponding baseline conditions of the structure. Storing the one or more baseline conditions of the structure corresponding to the at least one baseline structural interrogation can include storing the plurality of baseline conditions corresponding to the plurality of baseline structural interrogations.

Determining whether the difference between the one or more current conditions and the one or more baseline conditions satisfies the at least one threshold deviation criterion can include comparing, by the controller, the current conditions of the structure and each of the baseline conditions of the structure.

The method can further include storing, by the controller, a result of each of the at least one baseline structural interrogation of the structure, and comparing a result of the current structural interrogation to the result of one of the at least one baseline structural interrogation of the structure to identify the presence of structural damage of the structure.

Outputting the indication that the at least one threshold deviation criterion is not satisfied can include outputting an indication of an extent to which the at least one threshold deviation criterion is not satisfied.

Performing the at least one baseline structural interrogation of the structure in the one or more corresponding baseline conditions of the structure can include sensing, using the at least one sensor, the one or more corresponding baseline conditions.

The method can further include displaying the indication that the at least one threshold deviation criterion is not satisfied at a display device communicatively coupled with the controller.

The method can further include receiving, by the controller, the at least one threshold deviation criterion via a user interface communicatively coupled with the controller.

A system includes a physical structure, one or more sensors configured to sense current conditions of the structure, one or more transducers configured to perform a structural interrogation of the structure by inducing ultrasonic vibrations in the structure and sensing a resulting vibrational response of the structure, and a controller. The controller is configured to store one or more baseline conditions of the structure corresponding to at least one baseline structural interrogation of the structure, receive one or more current conditions of the structure sensed by the one or more sensors, and determine whether a difference between the one or more current conditions and the one or more baseline conditions satisfies at least one threshold deviation criterion. The controller is further configured to perform a current structural interrogation of the structure via the one or more transducers in response to determining that the difference between the one or more current conditions and the one or more baseline conditions satisfies the at least one threshold deviation criterion. The controller is further configured to output an indication that the at least one threshold deviation criterion is not satisfied in response to determining that the difference between the one or more current conditions and the one or more baseline conditions does not satisfy the at least one threshold deviation criterion.

The system of the preceding paragraph can optionally include, additionally and/or alternatively, any one or more of the following features, configurations, operations, and/or additional components:

The one or more sensors can include one or more temperature sensors. The one or more baseline conditions can include a temperature of the structure corresponding to the at least one baseline structural interrogation. The one or more current conditions can include a current temperature of the structure sensed by the one or more temperature sensors.

The one or more sensors can include one or more strain sensors. The one or more baseline conditions can include a strain of the structure corresponding to the at least one baseline structural interrogation. The one or more current conditions can include a current strain of the structure sensed by the one or more strain sensors.

The at least one threshold deviation criterion can include a maximum deviation between the one or more baseline conditions of the structure and the one or more current conditions of the structure.

The one or more baseline conditions of the structure corresponding to the at least one baseline structural interrogation can include a plurality of baseline conditions of the structure corresponding to a plurality of baseline structural interrogations of the structure. The controller can be configured to determine whether the difference between the one or more current conditions and the one or more baseline conditions satisfies the at least one threshold deviation criterion by comparing the current conditions of the structure and each of the baseline conditions of the structure.

The controller can be configured to store a result of each of the at least one baseline structural interrogation of the structure, and compare a result of the current structural interrogation to the result of one of the at least one baseline structural interrogation of the structure to identify the presence of structural damage of the structure.

The controller can be configured to output an extent by which the at least one threshold deviation criterion is not satisfied.

The controller can be configured to perform the at least one structural interrogation of the component via the one or more transducers and the one or more sensors.

The controller can be configured to present a graphical user interface at a display device, the graphical user interface configured to receive user input to request performance of the current structural interrogation.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method comprising:
    performing at least one baseline structural interrogation of a physical structure in one or more corresponding baseline conditions of the structure;
    storing, by a controller, the one or more baseline conditions of the structure corresponding to the at least one baseline structural interrogation;
    sensing, using at least one sensor, one or more current conditions of the structure;
    determining, by the controller, whether a difference between the one or more current conditions and the one or more baseline conditions satisfies at least one threshold deviation criterion, wherein the at least one threshold deviation criterion includes a maximum deviation between the one or more baseline conditions of the structure and the one or more current conditions of the structure;
    outputting, by the controller, either an indication that the at least one threshold deviation criterion is not satisfied in response to determining that the difference between the one or more current conditions and the one or more baseline conditions does not satisfy the at least one threshold deviation criterion or an indication that the at least one threshold deviation criterion is satisfied in response to determining that the difference between the one or more current conditions and the one or more baseline conditions does satisfy the at least one threshold deviation criterion;
    performing a current structural interrogation of the structure in response to determining that the difference between the one or more current conditions and the one or more baseline conditions satisfies the at least one threshold deviation criterion;
    storing, by the controller, a result of each of the at least one baseline structural interrogation of the structure; and
    comparing a result of the current structural interrogation to the result of one of the at least one baseline structural interrogation of the structure to identify the presence of structural damage of the structure.

2. The method of claim 1,
    wherein the one or more baseline conditions comprise a temperature of the structure corresponding to the at least one baseline structural interrogation; and
    wherein the one or more current conditions comprise a current temperature of the structure.

3. The method of claim 1,
    wherein performing the at least one baseline structural interrogation of the structure comprises performing a plurality of baseline structural interrogations of the structure in a plurality of corresponding baseline conditions of the structure;
    wherein storing the one or more baseline conditions of the structure corresponding to the at least one baseline structural interrogation comprises storing the plurality of baseline conditions corresponding to the plurality of baseline structural interrogations.

4. The method of claim 3,
    wherein determining whether the difference between the one or more current conditions and the one or more baseline conditions satisfies the at least one threshold deviation criterion comprises comparing, by the controller, the current conditions of the structure and each of the baseline conditions of the structure.

5. The method of claim 1,
    wherein outputting the indication that the at least one threshold deviation criterion is not satisfied comprises outputting an indication of an extent to which the at least one threshold deviation criterion is not satisfied.

6. The method of claim 1,
    wherein performing the at least one baseline structural interrogation of the structure in the one or more corresponding baseline conditions of the structure comprises sensing, using the at least one sensor, the one or more corresponding baseline conditions.

7. The method of claim 1, further comprising:
    displaying the indication that the at least one threshold deviation criterion is not satisfied at a display device communicatively coupled with the controller.

8. The method of claim 1, further comprising:
    receiving, by the controller, the at least one threshold deviation criterion via a user interface communicatively coupled with the controller.

9. A system comprising:
    a physical structure;
    one or more sensors configured to sense current conditions of the structure;
    one or more transducers configured to perform a structural interrogation of the structure by inducing ultrasonic vibrations in the structure and sensing a resulting vibrational response of the structure; and
    a controller configured to:
        store one or more baseline conditions of the structure corresponding to at least one baseline structural interrogation of the structure;
        receive one or more current conditions of the structure sensed by the one or more sensors;
        determine whether a difference between the one or more current conditions and the one or more baseline conditions satisfies at least one threshold deviation criterion, wherein the at least one threshold deviation criterion includes a maximum deviation between the one or more baseline conditions of the structure and the one or more current conditions of the structure;

output an indication either that the at least one threshold deviation criterion is not satisfied in response to determining that the difference between the one or more current conditions and the one or more baseline conditions does not satisfy the at least one threshold deviation criterion or that the at least one threshold deviation criterion is satisfied in response to determining that the difference between the one or more current conditions and the one or more baseline conditions does satisfy the at least one threshold deviation criterion;

perform a current structural interrogation of the structure via the one or more transducers in response to determining that the difference between the one or more current conditions and the one or more baseline conditions satisfies the at least one threshold deviation criterion;

store a result of each of the at least one baseline structural interrogation of the structure; and compare a result of the current structural interrogation to the result of one of the at least one baseline structural interrogation of the structure to identify the presence of structural damage of the structure.

10. The system of claim 9, wherein the one or more sensors comprise one or more temperature sensors;

wherein the one or more baseline conditions comprise a temperature of the structure corresponding to the at least one baseline structural interrogation; and wherein the one or more current conditions comprise a current temperature of the structure sensed by the one or more temperature sensors.

11. The system of claim 9, wherein the one or more sensors comprise one or more strain sensors;

wherein the one or more baseline conditions comprise a strain of the structure corresponding to the at least one baseline structural interrogation; and wherein the one or more current conditions comprise a current strain of the structure sensed by the one or more strain sensors.

12. The system of claim 9, wherein the one or more baseline conditions of the structure corresponding to the at least one baseline structural interrogation comprise a plurality of baseline conditions of the structure corresponding to a plurality of baseline structural interrogations of the structure; and wherein the controller is configured to determine whether the difference between the one or more current conditions and the one or more baseline conditions satisfies the at least one threshold deviation criterion by comparing the current conditions of the structure and each of the baseline conditions of the structure.

13. The system of claim 9, wherein the controller is configured to output an extent by which the at least one threshold deviation criterion is not satisfied.

14. The system of claim 9, wherein the controller is configured to perform the at least one structural interrogation of the component via the one or more transducers and the one or more sensors.

15. The system of claim 9, wherein the controller is configured to present a graphical user interface at a display device, the graphical user interface configured to receive user input to request performance of the current structural interrogation.

* * * * *